US011439792B2

(12) United States Patent
Haldis et al.

(10) Patent No.: US 11,439,792 B2
(45) Date of Patent: Sep. 13, 2022

(54) CATHETER WITH A SIDE PORT AND METHODS FOR USE THEREOF

(71) Applicant: Sanford Health, Sioux Falls, SD (US)

(72) Inventors: Thomas Haldis, Horace, ND (US); Alexander Drofa, West Fargo, ND (US)

(73) Assignee: Sanford Health, Sioux Falls, SD (US)

( * ) Notice: Subject to any disclaimer, the term of this patent is extended or adjusted under 35 U.S.C. 154(b) by 851 days.

(21) Appl. No.: 15/945,077

(22) Filed: Apr. 4, 2018

(65) Prior Publication Data

US 2018/0289926 A1 Oct. 11, 2018

Related U.S. Application Data

(60) Provisional application No. 62/481,844, filed on Apr. 5, 2017.

(51) Int. Cl.
*A61M 25/00* (2006.01)
*A61B 17/00* (2006.01)
(Continued)

(52) U.S. Cl.
CPC ... *A61M 25/0082* (2013.01); *A61B 17/00234* (2013.01); *A61M 25/003* (2013.01);
(Continued)

(58) Field of Classification Search
CPC ............ A61M 25/007; A61M 25/0662; A61M 25/003; A61M 25/0026; A61M 25/0102;
(Continued)

(56) References Cited

U.S. PATENT DOCUMENTS 4,682,978 A * 7/1987 Martin ................ A61M 5/1582
604/43
5,209,723 A * 5/1993 Twardowski ....... A61M 5/1582
604/103.07

(Continued)

FOREIGN PATENT DOCUMENTS

EP 2803340 A1 11/2014
WO 2008028102 A2 3/2008

OTHER PUBLICATIONS

International Search Report for corresponding PCT application No. PCT/US2018/026013, dated Jul. 6, 2018.

*Primary Examiner* — Katherine M Rodjom
(74) *Attorney, Agent, or Firm* — McDonnell Boehnen Hulbert & Berghoff LLP

(57) ABSTRACT

The present disclosure provides a catheter comprising: (a) a first tubular structure defining a first lumen, the first tubular structure having a first end and a second end, wherein the first end of the first tubular structure comprises a first opening, and wherein the second end of the first tubular structure comprises a second opening, (b) a second tubular structure defining a second lumen, the second tubular structure having a first end and a second end, wherein the second end of the second tubular structure comprises a third opening, and (c) a fourth opening positioned in a sidewall of the second tubular structure between the first end of the second tubular structure and the second end of the second tubular structure, wherein a first portion of the first tubular structure extends beyond the fourth opening, and wherein the second tubular structure is positioned adjacent to a second portion of the first tubular structure.

44 Claims, 5 Drawing Sheets

(51) Int. Cl.
*A61M 25/09* (2006.01)
*A61M 25/06* (2006.01)

(52) U.S. Cl.
CPC ...... *A61M 25/007* (2013.01); *A61M 25/0074* (2013.01); *A61M 25/0662* (2013.01); *A61M 25/09* (2013.01); *A61B 2017/00292* (2013.01); *A61B 2017/00862* (2013.01); *A61B 2017/00867* (2013.01); *A61B 2017/00942* (2013.01); *A61M 2025/0034* (2013.01); *A61M 2025/0037* (2013.01); *A61M 2025/0096* (2013.01); *A61M 2025/0681* (2013.01); *A61M 2205/0216* (2013.01); *A61M 2205/0266* (2013.01)

(58) Field of Classification Search
CPC .. A61M 2025/0037; A61M 2025/0025; A61M 2025/0681; A61M 2025/0687; A61M 2025/0034; A61B 2017/00323; A61B 2017/3447; A61B 2017/00292; A61B 17/00234
See application file for complete search history.

(56) References Cited

U.S. PATENT DOCUMENTS

| | | | | |
|---|---|---|---|---|
| 5,221,255 A * | 6/1993 | Mahurkar | ......... | A61M 25/0028 604/43 |
| 5,348,536 A * | 9/1994 | Young | ............... | A61M 25/0009 264/171.27 |
| 5,807,311 A * | 9/1998 | Palestrant | ........... | A61M 25/003 604/28 |
| 6,004,310 A * | 12/1999 | Bardsley | ............ | A61M 25/0009 604/524 |
| 9,597,084 B2 | 3/2017 | Zhadkevich | | |
| 2002/0107475 A1* | 8/2002 | Maginot | ........... | A61M 25/0028 604/48 |
| 2011/0098798 A1 | 4/2011 | Gurm | | |
| 2013/0158507 A1* | 6/2013 | Brown | ................ | A61M 25/007 604/506 |
| 2014/0018732 A1* | 1/2014 | Bagaoisan | ........ | A61M 25/0136 604/95.04 |
| 2015/0314111 A1 | 11/2015 | Solar | | |
| 2015/0366435 A1* | 12/2015 | Williams | ............. | A61B 1/0052 600/149 |

* cited by examiner

CATHETER WITH A SIDE PORT AND METHODS FOR USE THEREOF

RELATED APPLICATIONS

This application claims the benefit of priority to U.S. Provisional Application No. 62/481,844 entitled "Pigtail Catheter with a Side Port and Methods of Use," filed on Apr. 5, 2017, the contents of which are hereby incorporated by reference in its entirety.

BACKGROUND THE INVENTION

Endovascular procedures allow cardiovascular surgeries to be minimally invasive. Many procedures require access from the groin in the femoral artery. When performing interventions in the carotid artery or cerebral vasculature, the aortic arch is traversed with the wire and catheter. Aortic arches are classified as type I, type II, or type III. In a type III aortic arch, the ostium of the innominate artery is below the inner curve of the aortic arch. As a result, the difficulty increases for cannulation and performance of certain procedures within the great vessels off the aortic arch due to lack of backup support. In particular, work in distal craniocervical and thoracic vasculature may be difficult due to the prolapse of guiding catheters into the arch, particularly with type II and III aortic arches. In the setting of acute ischemic stroke, the time spent clearing the blockage needs to be minimized. Type III arches can take a significant amount of time to cannulate the great vessels of the arch. Also, during the process of trying to cannulate, many wire manipulations are made which can break thrombus loose from the arch effectively creating dangerous emboli. Therefore, an improved device for cannulating the proximal great vessels may be desired.

SUMMARY OF THE INVENTION

In a first aspect of the disclosure, a catheter is provided that includes: (a) a first tubular structure defining a first lumen, the first tubular structure having a first end and a second end, wherein the first end of the first tubular structure comprises a first opening, and wherein the second end of the first tubular structure comprises a second opening, (b) a second tubular structure defining a second lumen, the second tubular structure having a first end and a second end, wherein the second end of the second tubular structure comprises a third opening, and (c) a fourth opening positioned in a sidewall of the second tubular structure between the first end of the second tubular structure and the second end of the second tubular structure, wherein a first portion of the first tubular structure extends beyond the fourth opening, and wherein the second tubular structure is positioned adjacent to a second portion of the first tubular structure.

In a second aspect of the disclosure, a catheter system is provided that includes: (a) the catheter of the first aspect, wherein the catheter of the first aspect comprises a first catheter, and (b) a second catheter having a having a first end and a second end, wherein the second catheter has a diameter that is less than a diameter of the second tubular structure, and wherein the second catheter is positioned at least partially within the second lumen of the second tubular structure and is moveable relative to the second tubular structure.

In a third aspect of the disclosure, a method is provided that includes: (a) introducing a first guidewire into a first arterial configuration via arterial access, (b) loading the catheter according to the first aspect onto the first guidewire through the first lumen of the first tubular structure, (c) advancing the catheter along the first guidewire and introducing the catheter into the first arterial configuration, (d) introducing a second guidewire into the second lumen of the second tubular structure and through the fourth opening such that the second guidewire enters a second arterial configuration, and (e) advancing a guide catheter via the second guidewire into the second arterial configuration.

In a fourth aspect of the disclosure, a method is provided that includes: (a) introducing a first guidewire into a first arterial configuration via arterial access, (b) loading the catheter system according to the second aspect onto the first guidewire through the first lumen of the first tubular structure, (c) advancing the first catheter along the first guidewire and introducing the first catheter into the first arterial configuration, (d) introducing a second guidewire into the second lumen of the second tubular structure and through the fourth opening such that the second guidewire enters a second arterial configuration, and (e) advancing the second catheter via the second guidewire with respect to the first catheter and into the second arterial configuration.

These as well as other aspects, advantages, and alternatives, will become apparent to those of ordinary skill in the art by reading the following detailed description, with reference where appropriate to the accompanying drawings.

DETAILED DESCRIPTION OF THE INVENTION

Figure 1:
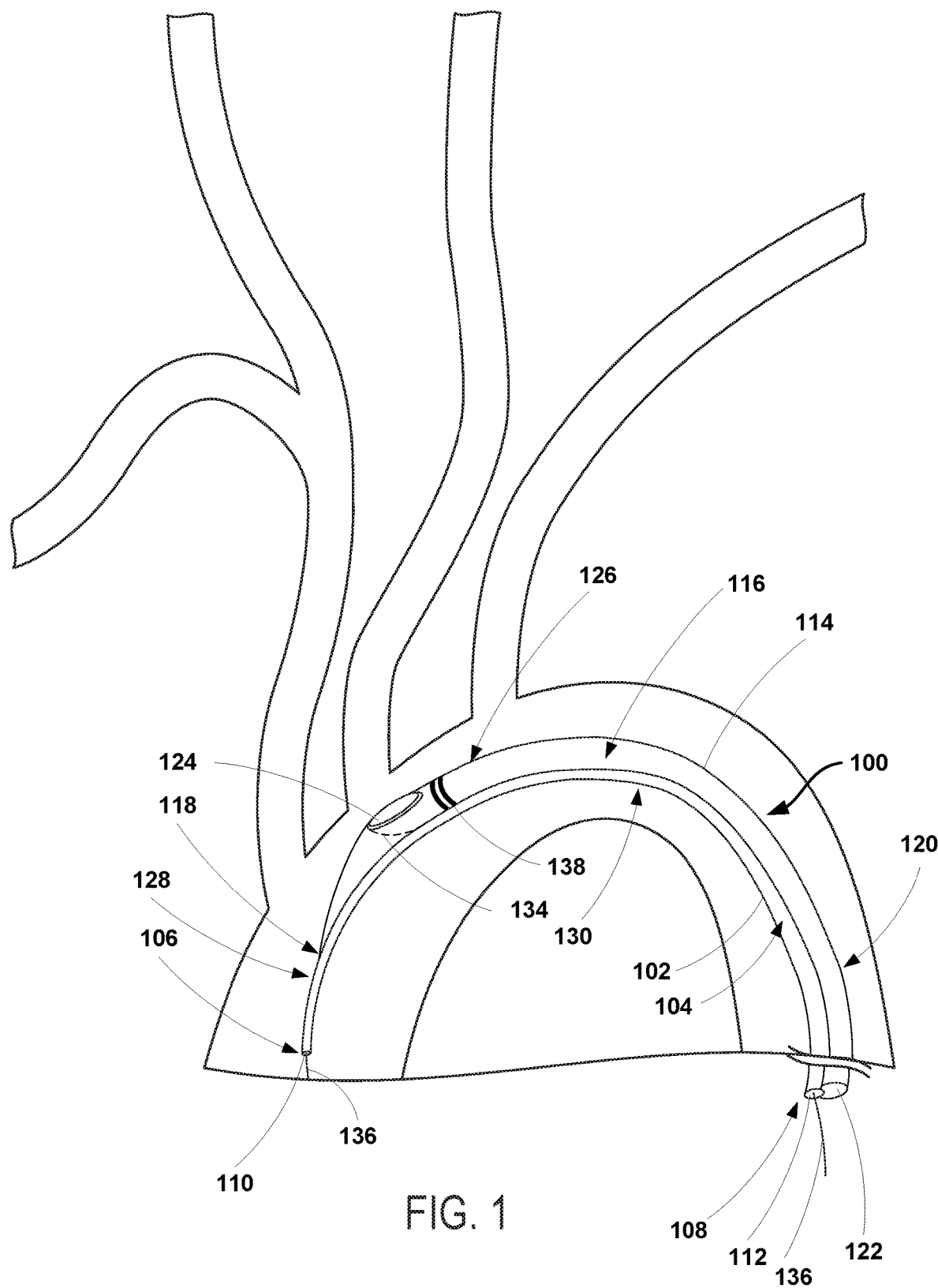
FIG. 1 is a side view of the catheter positioned in an aortic arch, according to an example embodiment.

Exemplary catheters, catheter systems and methods are described herein. The word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. Certain aspects of the catheters, catheter systems and methods can be arranged and combined in a wide variety of different configurations, all of which are contemplated herein.

Furthermore, the particular arrangements shown in the figures should not be viewed as limiting. Other embodiments may include more or less of each element shown in a given figure. Further, some of the illustrated elements may be combined or omitted. Yet further, an exemplary embodiment may include elements that are not illustrated in the figures.

As used herein, with respect to measurements, "about" means +/−5%.

As used herein, "coupled" means associated directly, as well as indirectly. For example, a member A may be directly associated with a member B, or may be indirectly associated therewith, e.g., via another member C. Not all relationships among the various disclosed elements are necessarily represented.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

Reference herein to "one embodiment" or "one example" means that one or more feature, structure, or characteristic described in connection with the example is included in at least one implementation. The phrases "one embodiment" or "one example" in various places in the specification may or may not be referring to the same example.

As used herein, a catheter, a catheter system, an element and a method "configured to" perform a specified function is indeed capable of performing the specified function without any alteration, rather than merely having potential to perform the specified function after further modification. In other words, a catheter, a catheter system, an element, and a method "configured to" perform a specified function is specifically selected, created, implemented, utilized, programmed, and/or designed for the purpose of performing the specified function. As used herein, "configured to" denotes existing characteristics of an a catheter, a catheter system, an element, and a method which enable the catheter, the catheter system, the element, and the method to perform the specified function without further modification. For purposes of this disclosure, the catheter, the catheter system, the element, and the method described as being "configured to" perform a particular function may additionally or alternatively be described as being "adapted to" and/or as being "operative to" perform that function.

As used herein, a "catheter" is an apparatus that is connected to a deployment mechanism and is configured to house a medical device that can be delivered over a guidewire. The catheter may include a guidewire lumen for over-the-wire guidance and may be used for delivering the medical device to a target lumen. A catheter can have braided metal strands within the catheter wall for increased structural integrity. The structural elements of the catheter tip can be bonded or laser welded to the braided strands of the catheter to improve the performance characteristics of the catheter tip.

As used herein, a "guidewire" is an elongated cable comprised of one or more biocompatible materials including metals and polymers. Guidewires may be used for selecting target lumens and guiding catheters to target deployment locations. Guidewires are typically defined as wires used independently of other devices that do not come as part of an assembly.

As used herein, "lumen" refers to a passage within an arterial or tubular structure, such as the cerebral or coronary arteries or a passage within the tubular structures or catheters through which the guidewire may be disposed.

As used herein, "deployment" refers to when a catheter has been positioned in the target lumen and is actively being used.

As used herein, "first end" and/or "first portion" refers to a distal end of the catheter, catheter system or component thereof, and "second end" and/or "second portion" refers to a proximal end of the catheter, catheter system or component thereof.

As used herein, "distal" with respect to a portion of the catheter means the end of the catheter (when in use) nearer the treatment zone (e.g., the aortic arch) of the subject and the term "proximal" means the portion of the catheter (when in use) further away from the targeted arterial configuration of the patient and nearer the access site and the operator.

As used herein, "arterial configuration" refers to any segment of the arterial tree.

As used herein, "French" refers to a unit of measurement for a catheter. A round catheter of 1 French has an external diameter of ⅓ mm, and therefore the diameter of a round catheter in millimeters can be determined by dividing the French size by 3.

In the following description, numerous specific details are set forth to provide a thorough understanding of the disclosed concepts, which may be practiced without some or all of these particulars. In other instances, details of known catheters, catheter systems and/or methods have been omitted to avoid unnecessarily obscuring the disclosure. While some concepts will be described in conjunction with specific examples, these examples are not intended to be limiting.

With respect to the Figures, FIG. 1 illustrates an example catheter 100. As shown in FIG. 1, the catheter 100 may include a first tubular structure 102 defining a first lumen 104, the first tubular structure having a first end 106 and a second end 108. The first end 106 of the first tubular structure 102 includes a first opening 110, and the second end 108 of the first tubular structure 102 includes a second opening 112. The catheter 100 also includes a second tubular structure 114 defining a second lumen 116. The second tubular structure 114 has a first end 118 and a second end 120. The second end 120 of the second tubular structure 114 includes a third opening 122. The second end 108 and corresponding second opening 112 of the first tubular structure 102 may remain outside of the body of the patient when the catheter 100 is in use to provide a working channel for a guidewire. Similarly, the second end 120 and corresponding third opening 122 of the second tubular structure 114 may remain outside of the body of the patient when the catheter 100 is in use to provide a working channel for a second guidewire and/or secondary catheter.

Figure 3:
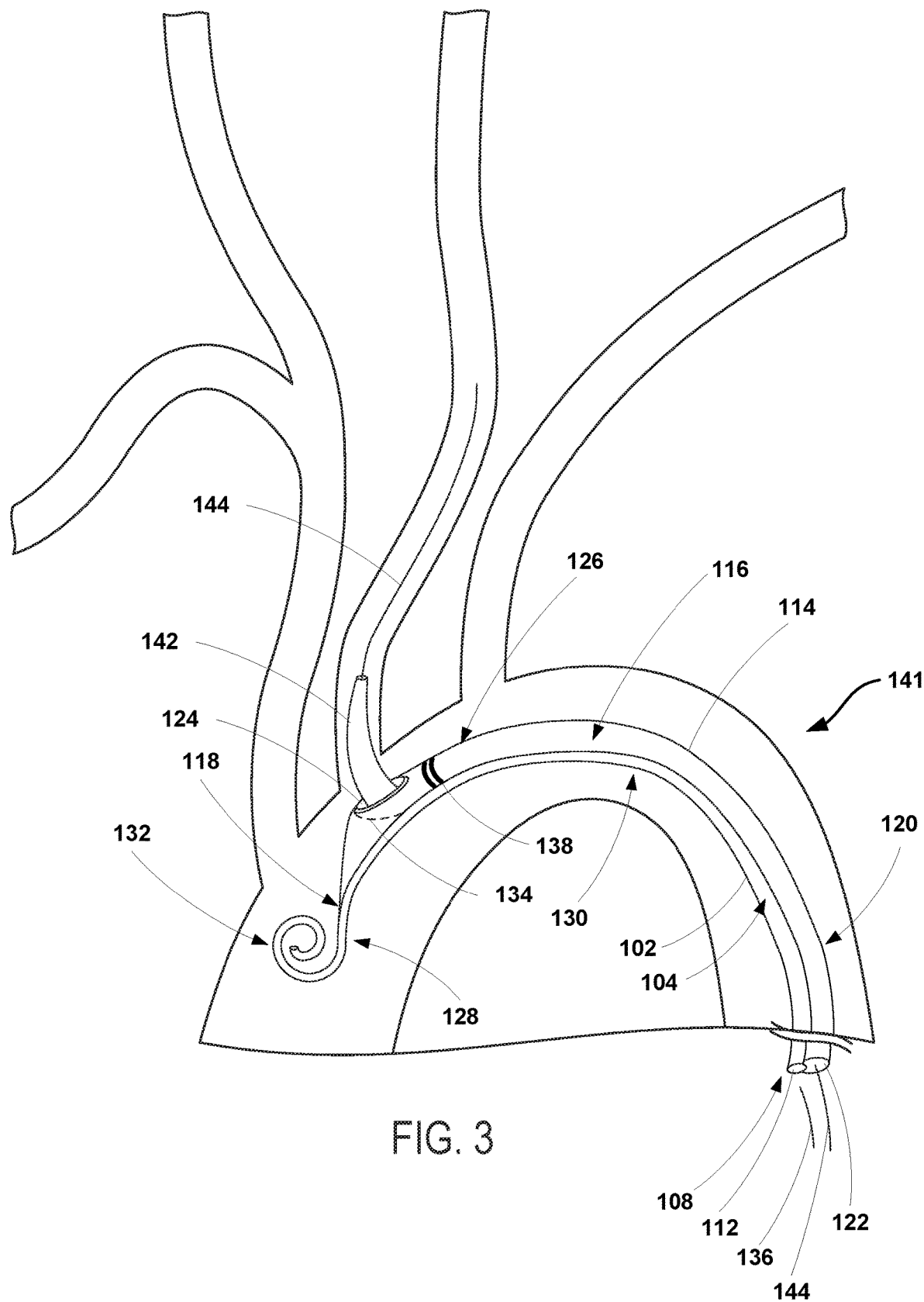
FIG. 3 is a side view of the catheter of FIG. 1 with the guidewire fully retracted from the first tubular structure and the guide catheter extending out of the fourth opening and into one of the great vessels, according to an example embodiment.

The catheter 100 further includes a fourth opening 124 positioned in a sidewall 126 of the second tubular structure 114 between the first end 118 of the second tubular structure 114 and the second end 120 of the second tubular structure 114. A first portion 128 of the first tubular structure 102 extends beyond the fourth opening 124. The second tubular structure 114 is positioned adjacent to a second portion 130 of the first tubular structure 102. In one example embodiment, the first portion 128 of the first tubular structure 102 may include a coilable portion 132 having shape memory, as best illustrated in FIG. 3. In other embodiments, the first portion 128 of the first tubular structure 102 may comprise any plurality of shapes and arrangements. As shown in FIG. 1, the second tubular structure 114 may taper from distal to the fourth opening 124 to the first portion 128 of the first tubular structure 102. Such a taper may provide a smooth transition from the larger diameter second tubular structure 114 to the smaller diameter first tubular structure 102. In addition, the tapered section may provide added stiffness and kink resistance to the portion of the catheter 100 positioned in the aortic arch when the catheter 100 is in use.

The first lumen 104 may have a length ranging from about 40 cm to about 200 cm. An inner lumen diameter of the second portion 130 of the first tubular structure 102 may range from about 0.018 mm to about 1 mm. The second tubular structure 114 may have a length ranging from about 35 cm to about 190 cm. A diameter of the second tubular structure 114 may range from about 5 French inner diameter to about 9 French inner diameter. The first portion 128 of the first tubular structure 102 may have a length ranging from about 5 cm to about 40 cm. A diameter of the first portion 128 of the first tubular structure 102 may have a range from about 0.018 mm to about 0.05 mm.

In one embodiment, a stiffness of the first tubular structure 102 is less than a stiffness of the second tubular structure 114. The stiffness may vary such that the first portion 128 of the first tubular structure 102 is relatively less stiff and atraumatic. In addition, a wire spine or core may provide stiffness around the aortic arch then down to the access site in the femoral artery. An area of the catheter 100 surrounding the fourth opening 124 may be reinforced or stiffer than the other components of the catheter 100 to provide kink resistance to the catheter 100.

In another example, the first tubular structure 102 includes a first material, and the second tubular structure 114 includes a second material that is different than the first material. In such an example, the first material may include an elastomer, a metal, a hydrophilic polymer, or a combination thereof, and the second material may comprise a different elastomer, a different metal, a different hydrophilic polymer, or a different combination thereof. In another example, a thickness of the walls of the first tubular structure 102 may be less than a thickness of the walls of the second tubular structure 114. In such an example, the first tubular structure 102 and the second tubular structure 114 may each include the same material(s), and the varying thicknesses of the walls result in different stiffnesses. In another example, as described above, the thickness of the walls first tubular structure 102 and the thickness of the walls of the second tubular structure 114 may be the same, while the difference in material(s) provides the difference in stiffness between the components. In another example, the first portion 128 of the first tubular structure 102 may have differential stiffness throughout; the second (i.e., proximal) end 108 may be stiff and gradually soften towards the first end 106 (i.e., distal tip).

Figure 2:
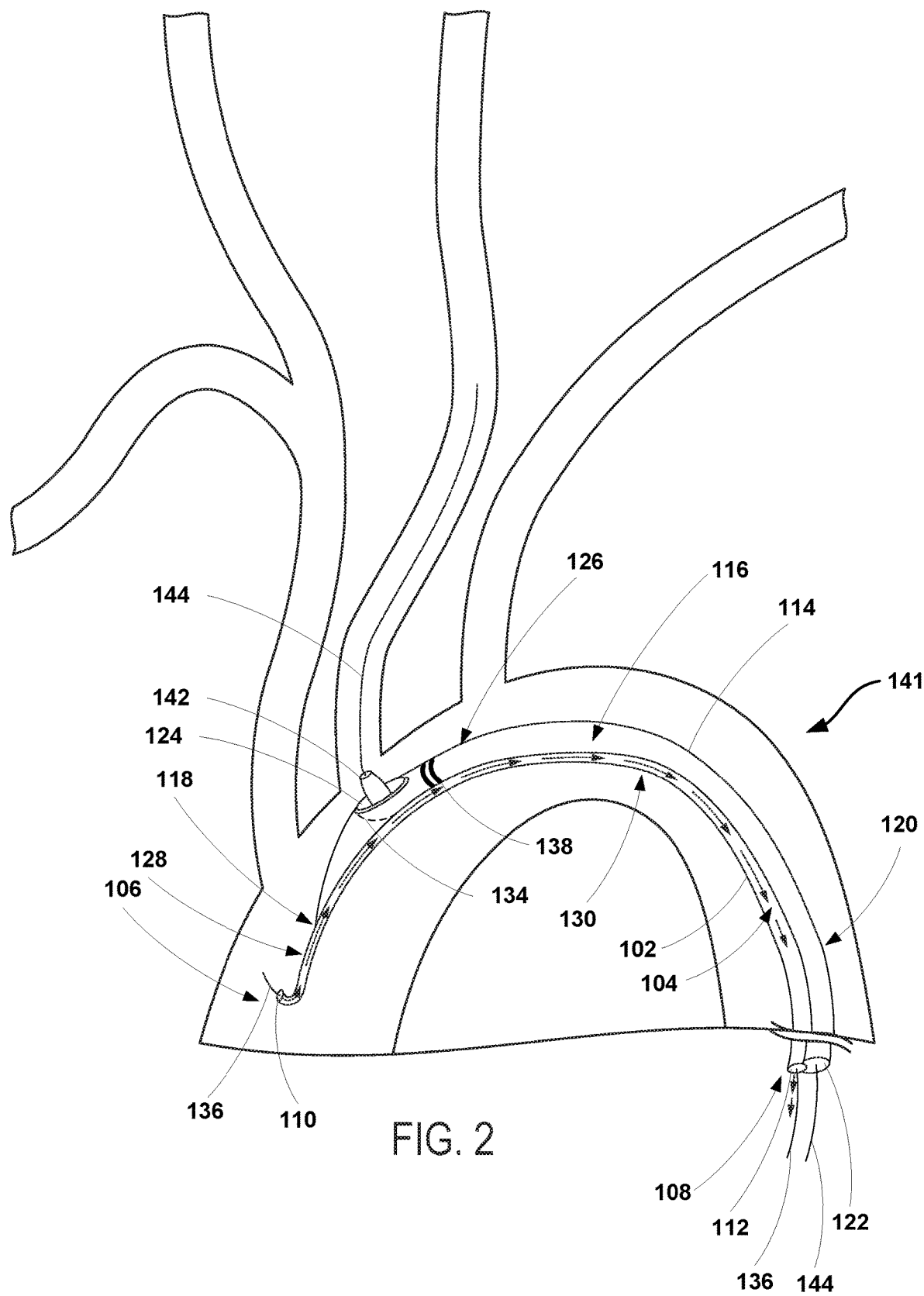
FIG. 2 is a side view of the catheter of FIG. 1 with a guidewire partially retracted from the first tubular structure and the guide catheter partially extending out of the fourth opening, according to an example embodiment.

As shown in FIGS. 1-3, a longitudinal axis of the second portion 130 of the first tubular structure 102 may be substantially parallel to a longitudinal axis of the second tubular structure 114. In addition, a longitudinal axis of the second lumen 116 may be perpendicular to a longitudinal axis of the fourth opening 124. The second tubular structure 114 may include a rounded surface 134 arranged to provide a rounded transition from the second tubular structure 114 to the fourth opening 124, as shown in FIGS. 1-3. As such, the rounded surface 134 may have a radius of curvature configured to guide a guidewire from the second lumen 116 out of the fourth opening 124. In another embodiment, the second tubular structure 114 may include an angled surface 134 arranged to provide an angled transition from the second tubular structure 114 to the fourth opening 124 to thereby guide a guidewire from the second lumen 116 out of the fourth opening 124.

In one embodiment, the first portion 128 of the first tubular structure 102 is tapered. Such an embodiment may be advantageous in that the first portion 128 of the first tubular structure 102 may be configured to sufficiently engage with a guidewire 136 that is positioned in the first lumen 104 of the first tubular structure 102. Such an arrangement may provide a fluid tight seal between the first opening 110 and the guidewire 136, such that fluid does not enter the first lumen 104 of the first tubular structure. The vessels taper as the catheter 100 travels more distal in the vascular tree. Therefore, a taper on the first portion 128 of the first tubular structure 102 may help negotiate bends and avoid snagging on vessel side branches. In another embodiment, the first portion 128 of the first tubular structure 102 includes a variable diameter. Such a configuration may help accommodate a guidewire 136 that is positioned in the first lumen 104 of the first tubular structure 102 without increasing the size of the catheter 100 and that would hereby decrease maneuverability and flexibility. In one example, the variable diameter of the first portion 128 of the first tubular structure 102 may be accomplished by including an expandable elastomer in that portion of the catheter 100. Such an expandable elastomer may have shape memory that biases the first portion 128 of the first tubular structure 102 to the variable diameter. In another example, the variable diameter of the first portion 128 of the first tubular structure 102 may be accomplished by including a C-shape 132 for that portion of the catheter 100, for example due to shape memory of the first portion 128 of the first tubular structure 102. In yet another example, the variable diameter of the first portion 128 of the first tubular structure 102 may be accomplished by both including an expandable elastomer having a C-shape 132 in that portion of the catheter 100. Other examples are possible as well.

In another embodiment, the coilable portion 128 includes a plurality of openings. The plurality of openings may be used for injection of IV contrast during the surgical procedure. In various non-limiting embodiments, the therapeutic may comprise sirolimus, heparin, and cell-based therapies; and antineoplastic, anti-inflammatory, antiplatelet, anticoagulant, antifibrin, antithrombin, antimitotic, antibiotic, vasodialate, antiallergic thrombolytic and antioxidant substances. The coilable portion 128 may be movable between an elongated orientation (shown in FIG. 1) and a coiled orientation (shown in FIG. 3) by removing a guidewire 136 from the first lumen 104. The shape memory properties of the material of the coilable portion 128 biases the coilable portion to the coiled orientation.

The catheter 100 may further include one or more visualization markers 138 positioned adjacent to the fourth opening 128. These markers 138 may be used to properly position the fourth opening 128 adjacent a target arterial configuration.

Figure 4:
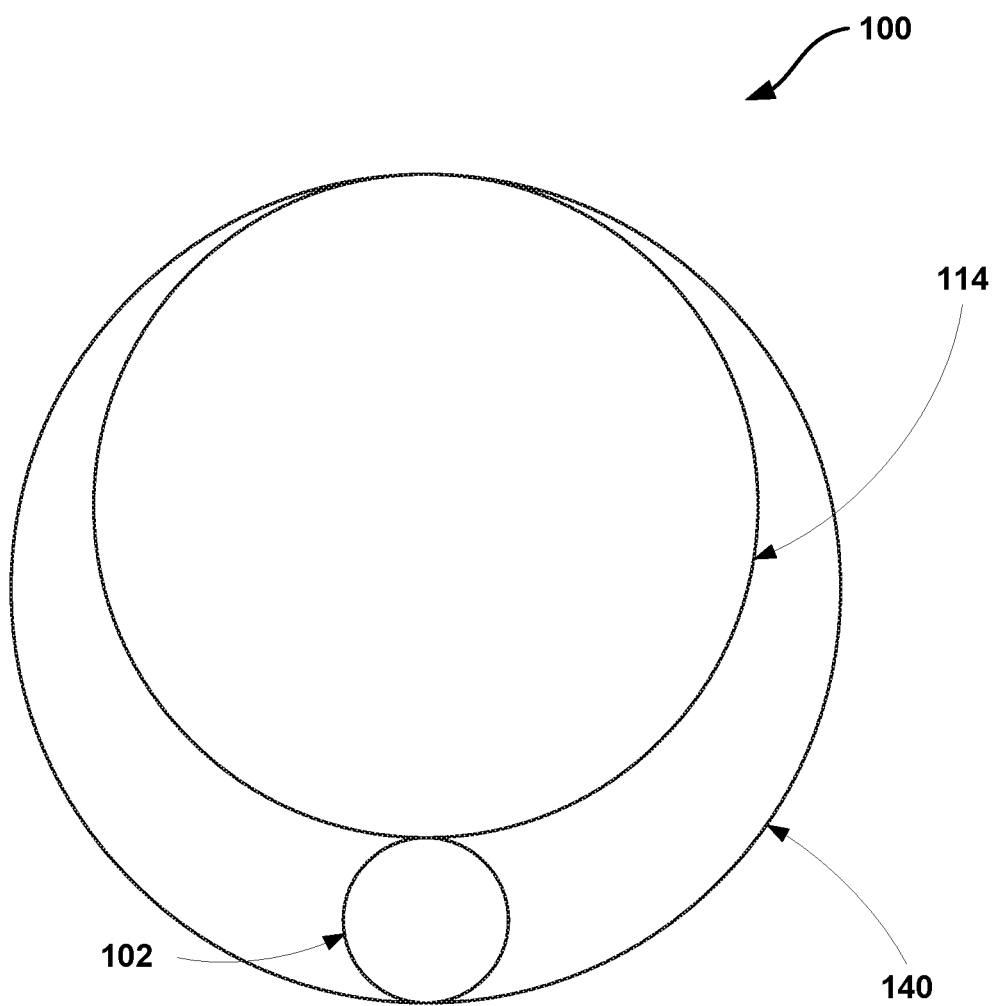
FIG. 4 is a side cross-sectional view of an example catheter, according to an example embodiment.

The catheter 100 may further include a plurality of metal strands arranged longitudinally or helically along at least a portion of a length of one or both of the first tubular structure 102 and the second tubular structure 114. In one example, the metal strands are braided. Braided metal strands may provide increased structural integrity. In another example, the metal strands may include strips. In one embodiment, a portion of the plurality of metal strands arranged along the second portion 130 of the first tubular structure 102 and the second tubular structure 114 are wider than a portion of the plurality of metal strands arranged along the first portion 128 of the first tubular structure 102. In another embodiment, a portion of the plurality of metal strands arranged along the second portion 130 of the first tubular structure 102 and the second tubular structure 114 are thicker than a portion of the plurality of metal strands arranged along the first portion 128 of the first tubular structure 102. In one example, as shown in FIG. 4, the catheter 100 may include an external housing 140 coupled to an exterior surface of the second portion 130 of the first tubular structure 102 and an exterior surface of the second tubular structure 114. In other words, the external housing 140 surrounds and encloses both the second portion 130 of the first tubular structure 102 and the second tubular structure 114. In such an example, the plurality of metal strands may be positioned along at least a portion of the exterior housing 140.

In another embodiment, a catheter system 141 is described. The catheter system 141 may include a first catheter 100, as described above in relation to FIGS. 1-4. The catheter system 141 may also include a second catheter 142 having a having a first end and a second end. The second catheter 142 may include a guide catheter, in one particular example. Such a guide catheter provides support for medical device advancement (e.g., stents, balloons, filters, etc.) in various arterial configurations. A guide catheter may be the conduit for device and wire transport as well as a vehicle for contrast injection. The second catheter 142 has a diameter that is less than a diameter of the second tubular structure 114, and the second catheter 142 is positioned at least partially within the second lumen 116 of the second tubular structure 114 and is moveable relative to the second tubular structure 114. The catheter system 141 may further include a wire 144 that has a first end and a second end, where the first end of the wire 144 is coupled to the second catheter 142. The wire 144 may include at least one braided wire, such as a braided stainless steel wire, for example. In another example, the wire 144 may be a nitinol wire. In another example, the wire 144 may be a solid or braided wire of any metal or metal alloy. In any of the above examples, the wire 144 may be positioned within a steel tube to provide structural support for the wire 144 when the wire is under compressive forces. In another example, the wire 144 may be positioned within a nitinol tube, thus preventing galvanic corrosion and also introducing a shape memory effect.

The catheter system 141 may include a mechanism to cause the second catheter 142 to move with respect to the first catheter 100. In one example, the second end of the wire 144 is coupled to a rotating threaded knob. In such an example, the wire 144 may be wound around the rotating threaded knob such that turning the rotating threaded knob clockwise and counter-clockwise causes the wire 144 to be wound and unwound around the rotating threaded knob to thereby cause the second catheter 142 to move with respect to the second tubular structure 114 of the first catheter 100. In another example, the second end of the wire 144 is coupled to a linear slide configured to move the wire 144 to cause the second catheter 142 to move with respect to the second tubular structure 114 of the first catheter 100. In another example, the second end of the wire 144 is coupled to a spooled wire system such that unwinding the spooled wire system advances the wire 144 to cause the second catheter 142 to move with respect to the second tubular structure 114 of the first catheter 100.

Figure 5:
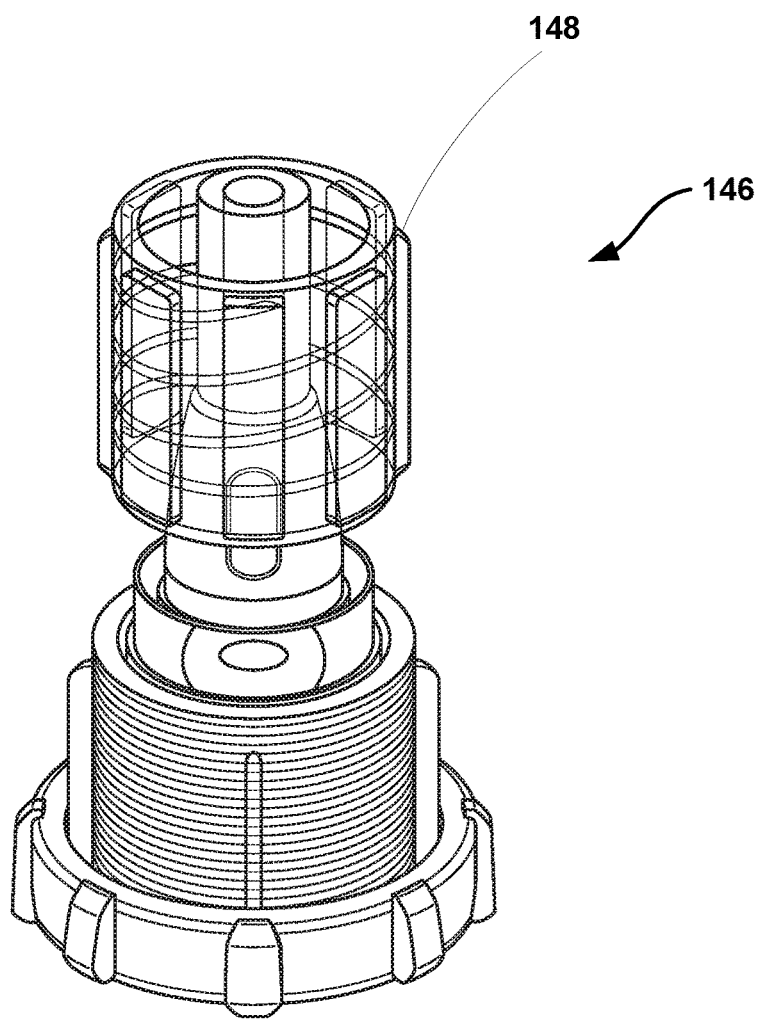
FIG. 5 is a side view of a locking system for a catheter system, according to an example embodiment.
Figure 6:
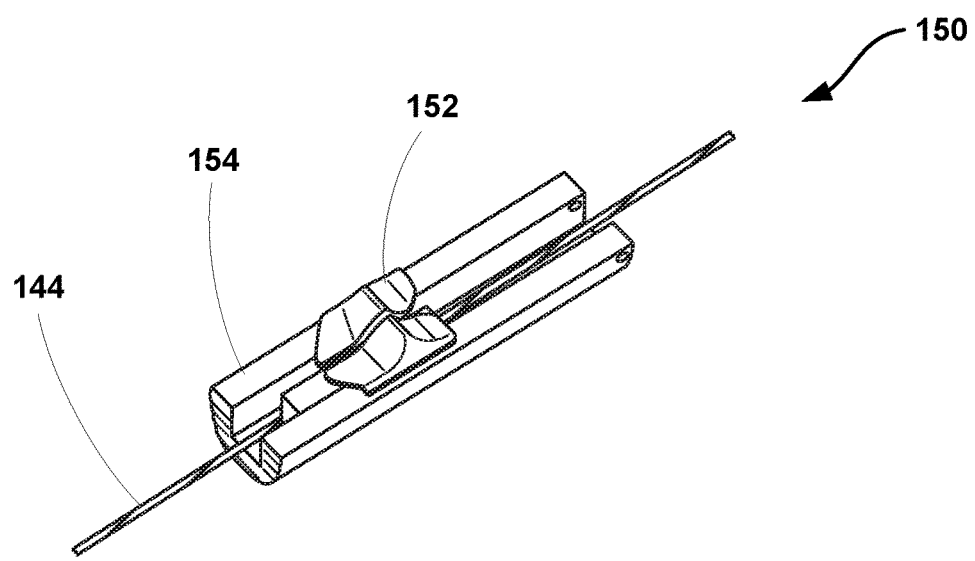
FIG. 6 is a side view of another locking system for the catheter system, according to an example embodiment.

The catheter system 141 may further comprise a locking system configured to lock the second catheter 142 in place. In one example, the locking system may include a friction or ratcheting break to prevent wire 144 and or wire advancement mechanism from moving spontaneously. In another example, the locking system may include a tightening nut in the case of the spooled wire system. When the tightening nut is tightened, the spool is unable to rotate, thereby preventing the wire 144 from being wound around the spool to thereby prevent the second catheter 142 from moving with respect to the first catheter 100. In another example, the locking system may include a tuohy-borst adapter 146 that can be tightened over an externalized part of the wire 144, as shown in FIG. 5. Such a tuohy-borst adapter 146 may also include a torque lock, locking nut, or a hemostatic valve. In use, the wire 144 may pass through a center of the tuohy-borst adapter 146, and a rotatable component 148 may be rotated to thereby tighten the tuohy-borst adapter 146 around the wire 144 to prevent the second catheter 142 from moving with respect to the first catheter 100. In yet another example, the locking system may include a linear press-and-advance system 150, as shown in FIG. 6. In such a configuration, the wire 144 is coupled to a slide 152, and the slide 152 is coupled to a housing 154. The housing 154 may remain stationary with respect to the first catheter 100, such that the second catheter 142 only moves with respect to the first catheter 100 when the slide 152 moves with respect to the housing 154.

The first catheter 100 may be in mechanical communication with the second catheter 142 in a number of arrangements. In one example, the first catheter 100 is in mechanical communication with the second catheter 142 via a gear system comprising a first gear coupled to the first catheter 100 and a second gear coupled to the second catheter 142. In such an example, an axis of rotation of the first gear may be positioned perpendicular to an axis of rotation of the second gear such that a rotation of the first gear translates to a linear movement of the second catheter 142 with respect to the first catheter 100. In another example, the first catheter 100 is in mechanical communication with the second catheter 142 via a rack and pinion system. Other example arrangements are possible as well. These examples also include a wire 144 that is configured to directly control the second catheter 142 (i.e., no additional mechanisms mediating the movement of the catheter are necessary).

In use, the disclosed examples may help simplify the process of cannulating the proximal great vessels. First, a guide wire 136 is used to advance the first catheter 100 into the ascending aorta. The first catheter 100 is then parked in the ascending aorta. Aortography is performed. The marker(s) 138 adjacent to the fourth opening 124 is then positioned at the opening of the vessel for which access is desired by rotating along its axis or advancing or retracting until the opening is aligned with the target vessel. Then a second wire 144 is used to cannulate the target vessel through the sideport 124 of the second lumen 116. Finally, a second catheter 142 or sheath or integrated slideguide mechanism (i.e., intermediate catheter) is advanced into the target vessel.

In operation, an example method includes introducing a first guidewire 136 into a first arterial configuration via arterial access. Then, the catheter 100 according to any of the embodiments described above is loaded onto the first guidewire 136 through the first lumen 104 of the first tubular structure 102. Next, the catheter 100 is advanced along the first guidewire 136 and the catheter 100 is introduced into the first arterial configuration. A second guidewire 144 is then introduced into the second lumen 116 of the second tubular structure 114 and through the fourth opening 124 such that the second guidewire 144 enters a second arterial configuration. And, advancing a guide catheter 142 via the second guidewire 144 into the second arterial configuration. The first arterial configuration may include an aortic arch, and the second arterial configuration may include one of a brachiocephalic artery, a right common carotid, a right or left vertebral artery, a left common carotid artery, or a left subclavian artery, renal arteries or spinal arteries.

In one embodiment, the method may further include retracting the catheter 100 while advancing the guide catheter 142 into the second arterial configuration. In another embodiment, the method may further include removing the first guidewire 136 from the first lumen 104 of the catheter 102. By removing the first guidewire 136, the coilable portion 132 may transition from an elongated orientation to a coiled orientation due to shape memory. In one example method, once the catheter 100 is positioned in the first arterial configuration and the guide catheter 142 is positioned in the second arterial configuration, a first filter is deployed through the first opening 110 of the first tubular structure 102 and into the first arterial configuration, and a second filter is deployed through the guide catheter 142 and into the second arterial configuration. Other arrangements are possible as well, including some arrangements that involve more or fewer steps than those described above, or steps in a different order than those described above.

In another embodiment, an example method may include introducing a first guidewire 136 into a first arterial configuration via arterial access. Then, the catheter system 141 according to any of the embodiments described above is loaded onto the first guidewire 136 through the first lumen 104 of the first tubular structure 102. Next, the first catheter 100 is advanced along the first guidewire 136 and is introduced into the first arterial configuration. A second guidewire 144 is introduced into the second lumen 116 of the second tubular structure 114 and through the fourth opening 124 such that the second guidewire 144 enters a second arterial configuration. And the second catheter 142 is advanced via the second guidewire 144 with respect to the first catheter 100 and into the second arterial configuration. The first arterial configuration may include an aortic arch, and the second arterial configuration may include one of a brachiocephalic artery, a right common carotid, a right or left vertebral artery, a left common carotid artery, a left subclavian artery, renal arteries, spinal arteries, pulmonary arteries, or a right ventricle.

In one embodiment, the method may further include retracting the first catheter 100 while advancing the second catheter 142 into the second arterial configuration. In one example method, once the first catheter 100 is positioned in the first arterial configuration and the second catheter 142 is positioned in the second arterial configuration, a first filter is deployed through the first opening 110 of the first tubular structure 102 and into the first arterial configuration, and a second filter is deployed through the second catheter 142 and into the second arterial configuration. Other arrangements are possible as well, including some arrangements that involve more or fewer steps than those described above, or steps in a different order than those described above.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the claims.

The invention claimed is:

1. A catheter comprising:
   a first tubular structure defining a first lumen, the first tubular structure having a first end and a second end, wherein the first end of the first tubular structure comprises a first opening, and wherein the second end of the first tubular structure comprises a second opening;
   a second tubular structure defining a second lumen, the second tubular structure having a first end and a second end, wherein the second end of the second tubular structure comprises a third opening; and
   a fourth opening positioned in a sidewall of the second tubular structure between the first end of the second tubular structure and the second end of the second tubular structure, wherein a first portion of the first tubular structure extends beyond the first end of the second tubular structure to the first opening, wherein a second portion of the first tubular structure extends from a proximal end of the first portion of the first tubular structure to the second opening, wherein the second portion of the first tubular structure is positioned adjacent to the second tubular structure, wherein the second tubular structure tapers from distal to the fourth opening to the proximal end of the first portion of the first tubular structure, and wherein a diameter of an entirety of the first tubular structure is less than a diameter of the second tubular structure.

2. The catheter of claim 1, wherein a stiffness of the first tubular structure is less than a stiffness of the second tubular structure.

3. The catheter of claim 1, wherein the first tubular structure comprises a first material, and wherein the second tubular structure comprises a second material that is different than the first material.

4. The catheter of claim 3, wherein the first material comprises an elastomer, a metal, a hydrophilic polymer, or a combination thereof.

5. The catheter of claim 3, wherein the second material comprises an elastomer, a metal, a hydrophilic polymer, or a combination thereof.

6. The catheter of claim 1, wherein a thickness of the first tubular structure is less than a thickness of the second tubular structure.

7. The catheter of claim 1, wherein a longitudinal axis of the second portion of the first tubular structure is parallel to a longitudinal axis of the second tubular structure.

8. The catheter of claim 1, wherein a longitudinal axis of the second lumen is perpendicular to a longitudinal axis of the fourth opening.

9. The catheter of claim 1, wherein the second tubular structure comprises an angled surface arranged to provide an angled transition from the second tubular structure to the fourth opening.

10. The catheter of claim 1, wherein the second tubular structure comprises a rounded surface arranged to provide a rounded transition from the second tubular structure to the fourth opening.

11. The catheter of claim 1, wherein the first portion the first tubular structure is tapered.

12. The catheter of claim 1, wherein the first portion of the first tubular structure includes a variable diameter.

13. The catheter of claim 1, wherein the first portion of the first tubular structure includes a coilable portion having shape memory.

14. The catheter of claim 13, wherein the coilable portion includes a plurality of openings in the first tubular structure.

15. The catheter of claim 13, wherein the coilable portion is movable between an elongated orientation and a coiled orientation by removing a guidewire from the first lumen.

16. The catheter of claim 1, further comprising one or more visualization markers positioned adjacent to the fourth opening.

17. The catheter of claim 1, wherein the catheter includes a plurality of metal strands arranged longitudinally or helically along at least a portion of a length of one or both of the first tubular structure and the second tubular structure.

18. The catheter of claim 17, wherein the plurality of metal strands comprises stainless steel, cobalt chromium, nitinol, or a combination thereof.

19. The catheter of claim 17, wherein the plurality of metal strands are braided.

20. The catheter of claim 17, wherein the plurality of metal strands comprise strips.

21. The catheter of claim 17, wherein a portion of the plurality of metal strands arranged along the second portion of the first tubular structure and the second tubular structure are wider than a portion of the plurality of metal strands arranged along the first portion of the first tubular structure.

22. The catheter of claim 17, wherein a portion of the plurality of metal strands arranged along the second portion of the first tubular structure and the second tubular structure are thicker than a portion of the plurality of metal strands arranged along the first portion of the first tubular structure.

23. The catheter of claim 1, wherein the first lumen has a length ranging from about 40 cm to about 200 cm.

24. The catheter of claim 1, wherein a diameter of the second portion of the first tubular structure has a range from about 0.018 mm to about 0.05 mm.

25. The catheter of claim 1, wherein the second tubular structure has a length ranging from about 35 cm to about 190 cm.

26. The catheter of claim 1, wherein a diameter of the second tubular structure has a range from about 5 French inner diameter to about 9 French inner diameter.

27. The catheter of claim 1, wherein the first portion of the first tubular structure has a length ranging from about 5 cm to about 40 cm.

28. The catheter of claim 1, wherein an inner lumen diameter of the first portion of the first tubular structure has a range from about 0.018 mm to about 1 mm.

29. The catheter of claim 1, wherein an external housing is coupled to an exterior surface of the second portion of the first tubular structure and an exterior surface of the second tubular structure.

30. A catheter system, comprising:
the catheter of claim 1, wherein the catheter of claim 1 comprises a first catheter; and
a second catheter having a having a first end and a second end, wherein the second catheter has a diameter that is less than a diameter of the second tubular structure, and wherein the second catheter is positioned at least partially within the second lumen of the second tubular structure and is moveable relative to the second tubular structure.

31. The catheter system of claim 30, further comprising a wire having a first end and a second end, wherein the first end of the wire is coupled to the second catheter.

32. The catheter system of claim 31, wherein the second end of the wire is coupled to a rotating threaded knob, and wherein the wire is wound around the rotating threaded knob such that turning the rotating threaded knob causes the wire to be wound around the rotating threaded knob to thereby cause the second catheter to move with respect to the second tubular structure.

33. The catheter system of claim 31, wherein the second end of the wire is coupled to a linear slide configured to move the wire to cause the second catheter to move with respect to the second tubular structure.

34. The catheter system of claim 31, wherein the second end of the wire is coupled to a spooled wire system such that unwinding the spooled wire system advances the wire to cause the second catheter to move with respect to the second tubular structure.

35. The catheter system of claim 30, further comprising a locking system configured to lock the second catheter in place.

36. The catheter system of claim 30, wherein the first catheter is in mechanical communication with the second catheter via a gear system comprising a first gear coupled to the first catheter and a second gear coupled to the second catheter.

37. The catheter system of claim 36, wherein an axis of rotation of the first gear is positioned perpendicular to an axis of rotation of the second gear such that a rotation of the first gear translates to a linear movement of the second catheter with respect to the second tubular structure.

38. The catheter system of claim 30, wherein the first catheter is in mechanical communication with the second catheter via a rack and pinion system.

39. A method comprising:
introducing a first guidewire into a first arterial configuration via arterial access;
loading the catheter according to claim 1 onto the first guidewire through the first lumen of the first tubular structure;
advancing the catheter along the first guidewire and introducing the catheter into the first arterial configuration;
introducing a second guidewire into the second lumen of the second tubular structure and through the fourth opening such that the second guidewire enters a second arterial configuration; and
advancing a guide catheter via the second guidewire into the second arterial configuration.

40. The method of claim 39, further comprising:
retracting the catheter while advancing the guide catheter into the second arterial configuration.

41. The method of claim 39, wherein the first arterial configuration comprises an aortic arch, and wherein the second arterial configuration comprises one of a brachiocephalic artery, a right common carotid, a right or left vertebral artery, a left common carotid artery, a left subclavian artery, renal arteries, spinal arteries, pulmonary arteries, or a right ventricle.

42. A method comprising:
introducing a first guidewire into a first arterial configuration via arterial access;
loading the catheter system according to claim 30 onto the first guidewire through the first lumen of the first tubular structure;
advancing the first catheter along the first guidewire and introducing the first catheter into the first arterial configuration;
introducing a second guidewire into the second lumen of the second tubular structure and through the fourth opening such that the second guidewire enters a second arterial configuration; and
advancing the second catheter via the second guidewire with respect to the first catheter and into the second arterial configuration.

43. The method of claim 42, further comprising:
retracting the first catheter while advancing the second catheter into the second arterial configuration.

44. The method of claim 42, wherein the first arterial configuration comprises an aortic arch, and wherein the second arterial configuration comprises one of a brachiocephalic artery, a right common carotid, a right or left vertebral artery, a left common carotid artery, a left subclavian artery, renal arteries, spinal arteries, pulmonary arteries, or a right ventricle.

* * * * *